United States Patent
Bernstein

(10) Patent No.: US 8,076,371 B2
(45) Date of Patent: Dec. 13, 2011

(54) GALLIUM COMPOSITIONS FOR THE TREATMENT OF LIVER CANCER AND METHODS OF USE

(76) Inventor: Lawrence R. Bernstein, Menlo Park, CA (US)

( * ) Notice: Subject to any disclaimer, the term of this patent is extended or adjusted under 35 U.S.C. 154(b) by 317 days.

(21) Appl. No.: 12/293,877

(22) PCT Filed: Mar. 8, 2007

(86) PCT No.: PCT/US2007/063582
§ 371 (c)(1),
(2), (4) Date: Mar. 3, 2009

(87) PCT Pub. No.: WO2008/036429
PCT Pub. Date: Mar. 27, 2008

(65) Prior Publication Data
US 2009/0208591 A1    Aug. 20, 2009

Related U.S. Application Data

(60) Provisional application No. 60/780,563, filed on Mar. 9, 2006.

(51) Int. Cl.
*A01N 55/02*    (2006.01)
*A61K 31/28*    (2006.01)
*C07F 5/00*     (2006.01)

(52) U.S. Cl. ............................... 514/492; 556/1
(58) Field of Classification Search ............ 514/492
See application file for complete search history.

(56) References Cited

U.S. PATENT DOCUMENTS 6,087,354 A       7/2000  Bernstein
2005/0054708 A1*  3/2005  Nichols et al. ............ 514/408
2005/0137185 A1*  6/2005  Lee et al. ................. 514/217

FOREIGN PATENT DOCUMENTS

SU    1235017 A   *   4/1987

OTHER PUBLICATIONS

Krecic-Shepard ME, Shepard DR, Mullet D, Apseloff G, Weissbrode SE, Gerber N (1999) Gallium nitrate suppresses the production of nitric oxide and liver damage in a murine model of LPS-induced septic shock. Life Sciences 65(13):1359-1371.

* cited by examiner

*Primary Examiner* — Sreeni Padmanabhan
*Assistant Examiner* — Layla Soroush

(57) ABSTRACT

Provided are compositions and methods to treat liver cancer and related disorders in human or veterinary individuals. Primary liver cancers, including those metastatic to other parts of the body, as well as cancers metastatic to the liver cancer, can be treated and/or prevented with the compositions and methods of the present invention. The methods comprise the administration of pharmaceutically acceptable gallium compositions, including gallium maltolate. Routes of administration include, without limitation, oral, intravenous, intratumoral, and into blood vessels as part of chemoembolization therapy. Some of the compositions and methods disclosed herein are applicable to cancers other than liver cancer.

3 Claims, No Drawings

GALLIUM COMPOSITIONS FOR THE TREATMENT OF LIVER CANCER AND METHODS OF USE

CROSS REFERENCE TO RELATED PATENT APPLICATIONS

This application claims priority under 35 U.S.C. §119(e) to U.S. Provisional Application No. 60/780,563, filed on Mar. 9, 2006, which is incorporated by reference in its entirety herein.

TECHNICAL FIELD

This invention relates generally to the treatment and prevention of liver cancer and related disorders. In particular, this invention relates to the use of pharmaceutically acceptable gallium compositions to treat and prevent liver cancer and of disorders that can, but do not necessarily, lead to liver cancer. Some of the compositions and methods of the invention are applicable to the treatment of cancers other than liver cancer.

BACKGROUND OF THE INVENTION

Primary liver cancer is one of the most common types of cancer in the world, with several hundred thousand new cases diagnosed annually. Of these, approximately 80% to 90% are hepatocellular carcinoma (HCC), also known as hepatoma. HCC is most prevalent in Asia and sub-Saharan Africa; in China alone there are more than 450,000 new cases per year, representing the fourth leading cause of death overall. HCC is the fastest increasing type of cancer in the United States: approximately 19,000 new cases are diagnosed annually, with resulting mortality of more than 16,000 per year.

Liver cancer commonly develops from liver cirrhosis, particularly that caused by hepatitis B or hepatitis C. The high incidence of liver cirrhosis and liver cancer found in Asia and Africa is due in large part to the high prevalence of hepatitis B and, increasingly, hepatitis C throughout these regions. The rising incidence of hepatitis C throughout the world is leading to an increase of liver cancer in other regions as well.

Cirrhosis due to causes other than hepatitis, including ingestion of ethanol and exposure to other organic solvents, can also lead to liver cancer. In addition, the ingestion of certain aflatoxins, which are toxins than can occur in stored grains and other foods as the result of fungal growth, is also associated with the development of liver cancer, as is the ingestion of other food- and water-borne carcinogens, including many drugs. Liver cancer may also arise from exposure to radiation, from mechanical trauma, and from other causes.

The current treatment of liver cancer is primarily surgical. If the cancer is localized to a particular region of the liver, and if that region can be safely removed, then surgical treatment may be successful. For the great majority of liver cancer patients, however, by the time the liver cancer is detected, too much of the liver is affected for surgical treatment to be safe and effective, and the cancer has commonly metastasized beyond the liver. Currently, these patients have few, if any, treatment options.

Gallium has repeatedly shown efficacy in treating certain cancers (Bernstein L R, PHARMACOL REV 50:665-682, 1998). In particular, gallium is known to be effective in treating lymphoma, multiple myeloma, prostate cancer, and bladder cancer. Topically or transdermally administered gallium is effective in treating hyperproliferative skin disorders such as psoriasis and skin cancer, and related dermatologic disorders (U.S. Pat. No. 5,747,482 to Bernstein). Gallium compounds, including gallium nitrate and gallium maltolate, also have anti-inflammatory activity; particular efficacy for gallium has been reported in animal models for inflammatory autoimmune diseases, such as rheumatoid arthritis (Delbarre F, Rabaud M, COMPTES RENDUS DE L'ACADÉMIE DES SCIENCES, Series D 283:1469-1472, 1976; Matkovic V et al., CURRENT THERAPEUTIC RESEARCH 50:255-267, 1991; U.S. Pat. No. 5,175,006), multiple sclerosis (Whitacre C et al., JOURNAL OF NEUROIMMUNOLOGY 39:175-182, 1992), uveitis (Lobanoff M C et al., EXPERIMENTAL EYE RESEARCH 65:797-801, 1997), and Type 1 diabetes (Flynn J O et al., DIABETES 41:38A, 1992). Gallium is also effective at inhibiting the loss of calcium from bone resulting from cancer, Paget's disease of bone, and other causes, and can be used to treat hypercalcemia associated with cancer. It is also known that gallium radioisotopes, such as $^{67}$Ga, concentrate in many types of neoplastic tissue, including liver cancer. Despite the use of gallium to treat and diagnose certain cancers and other diseases since the early 1970s, there has never been any suggestion to use gallium in the treatment of liver cancer or related disorders. It has now been found that gallium appears particularly effective at treating and preventing liver cancer.

SUMMARY OF THE INVENTION

Accordingly, it is a primary object of the invention to provide pharmaceutical compositions, methods, and drug delivery systems for treating or preventing liver cancer and related disorders.

In a methodological embodiment of the invention, a method for treating or preventing liver cancer is provided that comprises administering to an individual a therapeutically or prophylactically effective amount of gallium in the form of a pharmaceutically acceptable gallium-containing composition.

In another embodiment of the invention, there is provided a composition comprising a pharmaceutically acceptable gallium compound formulated for instillation into a tumor or other lesion.

In a further embodiment of the invention, there is provided a composition comprising a pharmaceutically acceptable gallium compound formulated for chemoembolization therapy.

In yet another embodiment of the invention, there is provided a method of treating cancer, comprising administration to an individual of a therapeutically effective amount of gallium in the form of a pharmaceutically acceptable gallium-containing composition by intratumoral instillation.

In yet a further embodiment of the invention, there is provided a method of treating cancer, comprising administering a therapeutically effective amount of a pharmaceutically acceptable gallium-containing composition to an individual, wherein the gallium-containing composition is administered to the individual as part of chemoembolization therapy.

In still another embodiment of the invention, there is provided an intratumoral administration method comprising administering a pharmaceutically acceptable gallium compound into one or more tumors of a patient afflicted with cancerous tumors, such as for example, hepatic tumors.

In still a further embodiment of the invention, there is provided a chemoembolization method comprising administering a pharmaceutically acceptable gallium compound into a hepatic artery or branches thereof to a patient suffering from liver cancer.

Additional objects, advantages, embodiments and novel features of the invention will be set forth in part in the description that follows, and in part will become apparent to those skilled in the art upon examination of the following, or may be learned by practice of the invention.

DETAILED DESCRIPTION OF THE INVENTION

Before the present compositions, methods, and drug delivery systems of the invention are disclosed and described, it is to be understood that this invention is not limited to specific formulations, i.e., specific carrier materials or the like, to specific dosage regimens, or to specific drug delivery systems, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a gallium compound" includes mixtures of such compounds; reference to "a carrier" includes mixtures of two or more carriers; and the like.

The term "patient" is meant to include a human or a veterinary patient. Within the context of the present invention, veterinary patients are intended to include both mammalian and non-mammalian veterinary patients, the latter including such veterinary patients as, for example, lizards and birds.

The terms "active agent," "drug," and "pharmacologically active agent" are used interchangeably herein to refer to a chemical material or compound that, when administered to an organism (human or animal, generally human) induces a desired pharmacologic effect, such as treatment of liver cancer.

The terms "to treat" and "treatment" as used herein encompass the usual meanings of these terms plus the usual meanings of the terms "to prevent" and "prevention." Thus, for example, "treatment" of liver cancer, as the term "treatment" is used herein, encompasses both prevention of liver cancer in a predisposed individual, such as an individual with liver cirrhosis, and treatment of liver cancer in an individual who has such a disease.

The term "effective" in reference to the amount of a drug means that there is a sufficient amount of a compound to provide the desired effect and performance at a reasonable benefit/risk ratio attending any medical treatment.

This invention includes compositions suitable for the administration of gallium, and devices and methods for using such compositions to treat liver cancer and related disorders.

Treatment is applicable to human and veterinary patients, including particularly mammals and birds. Mammalian veterinary subjects include, without limitation, dogs, cats, and members of the families Equidae, Bovidae, Caprinae, and Suidae. Veterinary subjects also include, without limitation, reptiles, amphibians, and fish.

The pharmaceutical compositions of the invention comprise a pharmaceutically acceptable carrier and a pharmaceutically acceptable gallium compound.

This invention involves the use of pharmaceutically acceptable gallium compounds to treat or prevent liver cancer and related disorders. Primary liver cancer includes, without limitation, hepatocellular carcinoma or hepatoma, cholangiocarcinoma, hepatoblastoma, and hepatic angiosarcoma. Related disorders include, without limitation, cirrhosis of the liver caused by disease or chemical exposure (including exposure to ethanol) such as for example, hepatitis B or hepatitis C, as well as benign liver tumors, including hemangiomas, hepatic adenomas, and focal nodular hyperplasias. Liver cancer that has metastasized to any part of the body may be treated by this invention. In addition, since numerous other types of cancer may also be treated effectively with gallium, many cancers metastatic to the liver may also be treated with this invention. The term "liver cancer" as used herein therefore encompasses both primary liver cancer, including metastases thereof, and cancer metastatic to the liver. Treatment or prevention may be in any human or veterinary patient; birds and mammals are preferred, with mammals more preferred, and humans particularly preferred.

Any pharmaceutically acceptable gallium compound may be used in this invention, by any medically acceptable route of administration. Gallium compounds usable in this invention include, without limitation, gallium nitrate, gallium sulfate, gallium citrate, gallium chloride, gallium complexes of 3-hydroxy-4-pyrones including gallium maltolate, gallium tartrate, gallium succinate, gallium gluconate, gallium palmitate, gallium 8-quinolinolate, gallium porphyrins including gallium(III) protoporphyrin IX, gallium transferrin, bis(2-acetylpyridine 4N-dimethylthiosemicarbazone)gallium (III)-gallium(III) tetrachloride, gallium pyridoxal isonicotinoyl hydrazone, gallium complexes of kenpaullone and its derivatives, and any other pharmaceutically acceptable gallium salts, organic salts, inorganic compounds, chelates, coordination compounds, and organometallic compounds. Gallium maltolate, tris(3-hydroxy-2-methyl-4H-pyran-4-onato)gallium, is a preferred gallium compound of the invention; this compound is described, for example, in U.S. Pat. No. 5,981,518 to Bernstein.

In one embodiment, the gallium compound is administered intravenously; for this purpose, gallium nitrate, gallium citrate, gallium palmitate, gallium porphyrins including gallium (III) protoporphyrin IX, gallium transferrin, bis(2-acetylpyridine 4N-dimethylthiosemicarbazone)gallium (III)-gallium (III) tetrachloride, pyridoxal isonicotinoyl hydrazone gallium (III), gallium malto late, and gallium complexes of kenpaullone and its derivatives, in a suitable pharmaceutically acceptable liquid formulation, are preferred, with citrate-buffered gallium nitrate particularly preferred.

In other embodiments, the gallium compound may be injected directly into one or more tumors and/or blood vessels that directly feed the one or more tumors. The gallium compound may be injected into one or more tumors via intratumoral administration, which includes without limitation intratumoral injection and/or instillation. Injection of the gallium compound into one or more blood vessels, such as a hepatic artery or branches thereof, is useful for procedures such as for example, chemoembolization therapy. Gallium compounds useful for intratumoral administration and/or chemoembolization therapy include without limitation any of the following gallium compounds: gallium nitrate, gallium citrate, gallium palmitate, gallium porphyrins including gallium(III) protoporphyrin IX, gallium transferrin, bis(2-acetylpyridine 4N-dimethylthiosemicarbazone)gallium (III)-gallium(III) tetrachloride, pyridoxal isonicotinoyl hydrazone gallium(III), gallium malto late, and gallium complexes of kenpaullone and its derivatives. Each of the gallium compounds set forth above is typically prepared in a suitable pharmaceutically acceptable formulation, such as a liquid or gel formulation. Gallium maltolate is a preferred gallium compound for use in intratumoral administration and chemoembolization therapy.

In a further embodiment, the gallium compound is administered orally. For this route of administration, preferred compounds are gallium nitrate, gallium citrate, gallium chloride, gallium 8-quinolinolate, and gallium maltolate; gallium maltolate is particularly preferred.

In other embodiments, the pharmaceutically acceptable gallium compound is administered transdermally, per rectum, vaginally, buccally, subcutaneously, intramuscularly, peritoneally, using depot formulations and/or devices, or by any other safe and effective route known in the art of drug delivery. For transdermal, rectal, vaginal, or buccal delivery, gallium maltolate and gallium 8-quinolinolate are preferred compounds, with gallium maltolate being particularly preferred. For subcutaneous, intramuscular, or peritoneal delivery, gallium nitrate, gallium citrate, gallium maltolate, and gallium 8-quinolinolate are preferred compounds, with citrate-buffered gallium nitrate being particularly preferred.

The gallium compositions of the invention may also be formulated using liposomes. Such formulations may be particularly advantageous for sustained release or delayed release compositions.

The gallium compound is administered in an amount effective to treat cancer or a related disorder. Such amounts, when administered systemically, generally result in plasma gallium concentrations of about 1 to 10,000 ng/mL, preferably about 100 to 5,000 ng/mL, and most preferably about 500 to 2,000 ng/mL.

When administered directly into a tumor or when used in chemoembolization therapy, the gallium concentrations of the injected liquid or gel are about 0.1 to about 10,000 µg/mL, preferably about 1.5 to 1,500 µg/mL, and more preferably about 100 to 1,000 µg/mL.

As an example of oral administration, gallium maltolate may be administered orally at a dose of about 50 to 5,000 mg/day, preferably about 200 to 3,000 mg/day, and more preferably about 300 to 2,000 mg/day, together with a pharmaceutically acceptable carrier. The dose may be administered in a single dose once per day, or in divided doses two or more times per day.

As an example of parenteral administration, citrate-buffered gallium nitrate is administered intravenously in a pharmaceutically acceptable intravenous liquid formulation, preferably as a slow infusion. The gallium nitrate is administered, for example, at a $Ga(NO_3)_3$ dose of about 10 to 1,000 $mg/m^2$/day, preferably about 100 to 500 $mg/m^2$/day, as a continuous intravenous infusion for about 1 to 10 days, preferably about 3 to 7 days. This dose may be repeated about every 1 to 12 weeks, preferably about every 2 to 4 weeks.

In one embodiment of the invention, a parenteral formulation of a gallium compound of the present invention is used in an improved intratumoral administration method by delivering the gallium compound directly into a tumor or lesion. In a preferred embodiment, the tumor or lesion is a hepatic tumor or lesion. In this method, the gallium compound, preferably gallium maltolate in a pharmaceutically acceptable liquid or gel carrier, is injected or otherwise instilled into the tumor or other lesion non-surgically or during surgery. The gel may contain pharmaceutically acceptable gel-forming materials such as, for example, soluble methylcellulose or carboxymethylcellulose, or purified bovine collagen. The gel delivery systems described, for example, in U.S. Pat. No. 6,630,168 to Jones et al.; U.S. Pat. No. 6,077,545 to Roskos et al.; U.S. Pat. No. 5,051,257 to Pietronigro; and RE 33,375 to Luck et al. may be used with the present invention. Additives, such as, for example, epinephrine as a vasoconstrictor to help retain the liquid or gel formulation within the tumor, may also be used.

In another embodiment of the invention, a parenteral formulation of a gallium compound, such as for example, gallium maltolate, is used in an improved chemoembolization method that uses the gallium compound to treat primary or metastatic liver cancer. In this method, the gallium compound, in a suitable pharmaceutically acceptable liquid or gel carrier, is injected into the hepatic artery or a branch of the hepatic artery feeding the region of the liver to be treated, together with standard embolization substances (such as certain oils and particulate matter; see, for example, Khayata et al., NEUROSURG CLIN N AM 5(3):475-484, 1994), which block arterial blood supply to the treated region. The rationale for this treatment is that normal liver tissue receives 75% of its blood supply from the portal vein and 25% from the hepatic artery, whereas liver tumors receive about 90% of their blood supply from the hepatic artery. Chemoembolization delivers a high dose of an antineoplastic drug directly to tumors, while simultaneously cutting off their subsequent arterial blood supply. Healthy liver tissue receives little exposure to the antineoplastic drug (such as gallium), and continues to receive the bulk of its normal blood supply, which comes from the portal vein. Chemoembolization formulations may include pharmaceutically acceptable oils, such as, for example, poppy seed oil or iodated poppy seed oil (e.g., lipiodol, to enhance radio-opacity). Biocompatible particulate matter may also be employed during chemoembolization; such particulate matter may comprise, for example, polyvinyl alcohol (PVA) (approximately 150-250 µm diameter) or tris-acryl gelatin microspheres (approximately 100-300 µm diameter). Typically, the gallium compound, such as gallium maltolate, will be administered in a water/oil emulsion; then, the particulate matter will be administered, commonly together with oil and/or radio-opaque material.

The practice of the present invention will employ, unless otherwise indicated, conventional techniques of drug formulation, particularly topical drug formulation, which are within the skill of the art. Such techniques are fully explained in the literature. See, for example, REMINGTON: THE SCIENCE AND PRACTICE OF PHARMACY (Univ. of the Sciences in Philadelphia, 2000) as well as Goodman & Gilman's THE PHARMACOLOGICAL BASIS OF THERAPEUTICS, 9th Ed. (New York: McGraw-Hill, 1996) and Ansel et al., PHARMACEUTICAL DOSAGE FORMS AND DRUG DELIVERY SYSTEMS, $6^{th}$ Ed. (Media, Pa.: Williams & Wilkins, 1995).

All patents, patent documents, and publications cited herein are hereby incorporated by reference in their entirety for their disclosure concerning any pertinent information not explicitly included herein.

It is to be understood that while the invention has been described in conjunction with the preferred specific embodiments thereof, the foregoing description, as well as the examples which follow, are intended to illustrate and not limit the scope of the invention. Other aspects, advantages and modifications will be apparent to those skilled in the art to which the invention pertains.

EXPERIMENTAL

The following examples are put forth so as to provide those of ordinary skill in the art with a complete disclosure and description of how to make and use the compositions of the invention. The examples are intended as non-limiting examples of the invention. While efforts have been made to ensure accuracy with respect to variables such as amounts, temperature, etc., experimental error and deviations should be taken into account. Unless indicated otherwise, parts are parts by weight, temperature is degrees Celsius, and pressure is at or near atmospheric. All components were obtained commercially unless otherwise indicated.

EXAMPLE 1

In Vitro Activity of Gallium Maltolate and Gallium Nitrate on Human Hepatocelluar Carcinoma Cells The activity of gallium maltolate and gallium nitrate was studied in vitro on several human hepatocellular carcinoma (HCC) cell lines (Hep3B, HepG2, SNU475, and Hep 40). Further information on these experiments is reported by Chua et al., Anticancer Research 26:1739-1744, 2006.

Methods

Proliferation assay: Cells were incubated at 37° C. overnight before addition of gallium maltolate or gallium nitrate (test compounds) in the desired concentration ranges. The cells were then exposed to the test compounds for six days. Colorimetric assessment of cell viability was then performed at 490 nm on a plate reader. Assays were done in triplicate, with n=4 for each experiment.

Assessment of apoptotic cell morphology: After six days exposure to gallium maltolate at either 10 µM or 30 µM, cells were fixed using absolute methanol at −20° C. for 10 min, then stained with hematoxylin and eosin. Cell morphology was then observed with a light microscope.

Immunoblotting: Cells were exposed to 10 µM or 30 µM gallium maltolate for six days; whole cell lysates were then prepared and total protein quantified using the Bradford Assay. Approximately 20 µg of protein was electrophoresed on pre-cast gels and transferred onto PVDF membranes. Nonspecific sites were blocked by incubation with 5% non-fat milk in TBS-1% Tween solution for 1 hr at room temperature. Proteins were then detected with specific antibodies against CD71 (transferrin receptor 1) or PARP at recommended dilutions, followed by appropriate HRP-conjugated secondary antibodies.

Gene expression data analysis: Gene expression data on 75 liver tumor and 72 non-tumor liver tissues were retrieved from the Stanford Microarray Database and analyzed by the web-based microarray data analysis program GABRIEL (Genetic Analysis By Rules Incorporating Expert Logic).

Results and Discussion

Antiproliferative activity: Gallium maltolate and gallium nitrate were antiproliferative to all four HCC cell lines tested, with IC50 values ranging from 25 to 35 µM for gallium maltolate and 60 to 250 µM for gallium nitrate. Although both compounds had antiproliferative activity, gallium maltolate was significantly more potent.

Induction of apoptosis by gallium maltolate: Gallium maltolate at 30 µM produced cellular morphology indicative of apoptosis in all four HCC cell lines studied. In addition, the poly(ADP-ribose) polymerase (PARP) assay for apoptosis was positive in HCC cell lines Hep 3B, Hep 40, and SNU475; the HepG2 cells appeared to lack PARP, suggesting that apoptosis was mediated by other pathways.

Dose-dependent regulation of transferrin receptor expression by gallium maltolate: Western blotting results showed that all four studied HCC cell lines expressed readily detectable levels of CD71 (transferrin receptor 1), with Hep 40 expressing it at higher levels than the others. Following six-day exposure to 10 µM or 30 µM gallium maltolate, the protein level of CD71 demonstrated a dose-dependent increase in all four HCC cell lines. The increased expression of CD71 following gallium exposure sets up a self-destructive loop, as it promotes further gallium uptake through CD71, which ultimately inhibits cell division, leading to cell death.

Over-expression of RRM2 in HCC: Gallium is known to substitute for $Fe^{3+}$ in the M2 subunit of ribonucleotide reductase (RRM2). This substitution disables ribonucleotide reductase and consequently prevents the synthesis of DNA. RRM2 (t-score=8.51) was among the top two percent of genes with a t-score greater than 2, suggesting that it was consistently (65 of 75 tumor samples) and significantly differentially up-regulated in tumor versus non-tumor liver tissue. RRM2 thus appears to be a good, selective target for anti-HCC therapy. Further analysis showed that RRM2 expression was highly correlated (0.843) with tumor stage, further implying that RRM2 is a good target for therapy, since most patients are diagnosed at late stages of the disease.

EXAMPLE 2

Intratumoral Gallium Maltolate Formulation

The following formulation may be used for intratumoral administration:

| | |
|---|---|
| Gallium maltolate | 1.0% w/v |
| Epinephrine | 0.1% w/v |
| Carboxymethylcellulose | 0.6% w/v |
| Normal saline solution | 98.3% v/v |

The gallium maltolate and epinephrine are first dissolved in the normal saline solution. The carboxymethylcellulose is then slowly added to the resulting solution, with continuous stirring, until a homogeneous gel is produced.

A recommended carboxymethylcellulose for use in the formulation of the liquid oral dosage form described herein is AQUALON® sodium carboxymethylcellulose gum, grade 7M2F, X grind (fine), viscosity of 2% solution approximately 150-200 cps (Hercules, Inc., Wilmington, Del.).

EXAMPLE 3

Gallium Maltolate Formulation for Use in Chemoembolization

The following formulation may be used for chemoembolization:

| | |
|---|---|
| Gallium maltolate | 1.0% w/v |
| Lipidiol | 49.9% v/v |
| Normal saline solution | 50.0% v/v |

The gallium maltolate is first dissolved in the normal saline solution. The resulting solution is then emulsified to a homogeneous emulsion with the lipidiol.

Following administration of this formulation, as into a branch of the hepatic artery feeding a tumor, embolic particles (EMBOSPHERE® tris acryl gelatin particles approximately 100-300 µm in diameter; BioSphere Medical, Rockland, Mass.) are injected, in a manufacturer-prefilled syringe comprising calibrated spheres in approximately 5 mL saline solution, reconstituted with 5 mL contrast medium (Omnipaque 350; Amersham, Piscataway, N.J.).

I claim:

1. A method for treating hepatocellular carcinoma in an individual afflicted with such a condition, comprising administering to the individual a therapeutically effective amount of a composition consisting essentially of a pharmaceutically acceptable carrier and a pharmaceutically acceptable gallium maltolate.

2. The method of claim 1, wherein the composition is administered orally.

3. A method for treating hepatocellular carcinoma in an individual afflicted with such a condition, comprising administering orally to the individual a therapeutically effective amount of a composition consisting essentially of gallium maltolate and a pharmaceutically acceptable carrier.

* * * * *